(12) United States Patent
Hanashiro et al.

(10) Patent No.: US 11,931,439 B2
(45) Date of Patent: Mar. 19, 2024

(54) CUSTOMIZED COLOR SHADE SUNSCREEN PRODUCTS AND PREPARATION THEREOF

(71) Applicant: L'Oreal, Paris (FR)

(72) Inventors: Tassia Hanashiro, Rio de Janeiro (BR); Angeles Fonolla-Moreno, Rio de Janeiro (BR); Renata Souto Maior Afonso Ferreira, Rio de Janeiro (BR)

(73) Assignee: L'Oreal, Paris (FR)

( * ) Notice: Subject to any disclaimer, the term of this patent is extended or adjusted under 35 U.S.C. 154(b) by 231 days.

(21) Appl. No.: 17/255,585

(22) PCT Filed: Jun. 29, 2018

(86) PCT No.: PCT/BR2018/050221
§ 371 (c)(1),
(2) Date: Dec. 23, 2020

(87) PCT Pub. No.: WO2020/000071
PCT Pub. Date: Jan. 2, 2020

(65) Prior Publication Data
US 2021/0220240 A1    Jul. 22, 2021

(51) Int. Cl.
*A61K 8/29*     (2006.01)
*A61K 8/04*     (2006.01)
*A61K 8/42*     (2006.01)
*A61Q 17/04*    (2006.01)

(52) U.S. Cl.
CPC ............... *A61K 8/29* (2013.01); *A61K 8/04* (2013.01); *A61K 8/42* (2013.01); *A61Q 17/04* (2013.01); *A61K 2800/43* (2013.01); *A61K 2800/524* (2013.01)

(58) Field of Classification Search
None
See application file for complete search history.

(56) References Cited

U.S. PATENT DOCUMENTS 5,785,960 A    7/1998  Rigg et al.

OTHER PUBLICATIONS

PCT International Search Report for PCT/BR2018/050221 dated Mar. 4, 2019.

*Primary Examiner* — Nannette Holloman
(74) *Attorney, Agent, or Firm* — McNees Wallace & Nurick LLC

(57) ABSTRACT

A product for providing a customized color shade sunscreen product to match a skin tone of a subject is provided. The product comprises a color dose formulation, an instruction and optionally a sunscreen. The color dose formulation has high concentration of pigments and is suitable for being mixed with a sunscreen to prepare a customized color shade sunscreen product. Also is a method of preparing a customized color shade sunscreen product to match a skin tone of a subject. Such method comprises mixing a selected color dose formulation with a sunscreen. The color dose formulations may be selected from six color shade compositions that offer color shades suitable for all skin tones. The customized color shade sunscreen product may provide a sensorial benefit such as dry touch, good spreadability, no white residues, oil control and UV protection and visible light.

40 Claims, No Drawings

CUSTOMIZED COLOR SHADE SUNSCREEN PRODUCTS AND PREPARATION THEREOF

FIELD OF THE INVENTION

The invention relates to customized color shade sunscreen products to match a skin tone of a subject and preparation thereof.

BACKGROUND OF THE INVENTION

Widely used to protect skin from damages caused by the sun, untinted sunscreens are a big part of market. Due to the big demand for multibenefits products, bringing different benefits in the same product, the consumers are always looking for products that provide high sun protection with makeup effect and good coverage and fit with diverse skin tones. It is a big challenge to develop a sunscreen with high SPF and high concentration of pigments mainly because of the stability of formulas and matching correctly the skin tone with the color product. There is a need for stable color shade sunscreen products adapted to all skin tones without compromising desirable sunscreen benefits.

SUMMARY OF THE INVENTION

The present invention relates to the use of high concentration of pigments with different shades to customize sunscreen products for all skin tones, providing a very good coverage and skin sensorial benefits such as dry touch, good spreadability and oil control without white residues, and preparation thereof. The inventors have unexpectedly discovered that mixing high concentration of pigments with sunscreen products created customized tinted sunscreen products with high coverage and a perfect range of color shades to fit all skin tones without an impact on stability of the sunscreen products and other benefits such as high Sun Protection Factor (SPF) values, antioxidant effects, infrared protection and visible light protection.

A product for providing a customized color shade sunscreen product, comprising a color dose formulation and an instruction, is provided. The color base composition is selected to match a skin tone of a subject from the group consisting of six color shade compositions: a first color shade composition comprising 26-27 wt % of a first pigment, 0.7-0.8 wt % of a second pigment, 0.2-0.3 wt % of a third pigment, and 5-6 wt % of a fourth pigment; a second color shade composition comprising 26-27 wt % of the first pigment, 0.8-0.9 wt % of the second pigment, 0.1-0.2 wt % of the third pigment, and 2-3 wt % of the fourth pigment; a third color shade composition comprising 22-23 wt % of the first pigment, 1-2 wt % of the second pigment, 0.5-0.6 wt % of the third pigment, and 8-9 wt % of the fourth pigment; a fourth color shade composition comprising 18-19 wt % of the first pigment, 1-2 wt % of the second pigment, 0.5-1.0 wt % of the third pigment, and 12-13 wt % of the fourth pigment; a fifth color shade composition comprising 6-7 wt % of the first pigment, 5-6 wt % of the second pigment, 1-2 wt % of the third pigment, and 19-20 wt % of the fourth pigment; and a sixth color shade composition comprising 8-9 wt % of the second pigment, 6-7 wt % of the third pigment, and 14-15 wt % of the fourth pigment. The first pigment comprises titanium oxide anatase coated with stearoyl aluminum glutamate. The second pigment comprises red iron oxide coated with stearoyl aluminum glutamate. Third pigment comprises black iron oxide coated with aluminum stearoyl glutamate. The fourth pigment comprises yellow iron oxide wrapped with aluminum stearoyl glutamate. The color dose formulation comprises at least 28 wt % totally of the pigments. The color dose formulation is suitable for being mixed with a sunscreen, which may be untinted or tinted, to prepare a customized color shade sunscreen product. The instruction comprises mixing the selected color dose formulation with the sunscreen. The instruction may further comprise selecting the color dose formulation to match the skin tone of the subject. As a result, a customized color shade sunscreen product is prepared and matches the skin tone of the subject.

A product for providing a customized color shade sunscreen product, comprising a color dose formulation, a sunscreen, which may be tinted or untinted, and an instruction, is also provided. The color base composition is selected to match a skin tone of a subject from the group consisting of six color shade compositions: a first color shade composition comprising 26-27 wt % of a first pigment, 0.7-0.8 wt % of a second pigment, 0.2-0.3 wt % of a third pigment, and 5-6 wt % of a fourth pigment; a second color shade composition comprising 26-27 wt % of the first pigment, 0.8-0.9 wt % of the second pigment, 0.1-0.2 wt % of the third pigment, and 2-3 wt % of the fourth pigment; a third color shade composition comprising 22-23 wt % of the first pigment, 1-2 wt % of the second pigment, 0.5-0.6 wt % of the third pigment, and 8-9 wt % of the fourth pigment; a fourth color shade composition comprising 18-19 wt % of the first pigment, 1-2 wt % of the second pigment, 0.5-1.0 wt % of the third pigment, and 12-13 wt % of the fourth pigment; a fifth color shade composition comprising 6-7 wt % of the first pigment, 5-6 wt % of the second pigment, 1-2 wt % of the third pigment, and 19-20 wt % of the fourth pigment; and a sixth color shade composition comprising 8-9 wt % of the second pigment, 6-7 wt % of the third pigment, and 14-15 wt % of the fourth pigment. The first pigment comprises titanium oxide anatase coated with stearoyl aluminum glutamate. The second pigment comprises red iron oxide coated with stearoyl aluminum glutamate. Third pigment comprises black iron oxide coated with aluminum stearoyl glutamate. The fourth pigment comprises yellow iron oxide wrapped with aluminum stearoyl glutamate. The color dose formulation comprises at least 28 wt % totally of the pigments. The instruction comprises selecting the color dose formulation to match a skin tone of a subject, and mixing the selected color dose formulation with the sunscreen by, for example, adding 2-4 drops of the color shade formulation into the sunscreen. The instruction may further comprise selecting the color dose formulation to match the skin tone of the subject. As a result, whereby a customized color shade sunscreen product is prepared and matches the skin tone of the subject.

The six color shade compositions may offer color shades suitable for all skin tones. The six color shade compositions may offer color shades suitable for all six skin phototypes according to the Fitzpatrick scale.

The customized color shade sunscreen product may provide a sensorial benefit. The sensorial benefit may be dry touch, good spreadability, no white residues, oil control or a combination thereof. The color dose formulation may be a cream, paste or fluid dispersion. The color dose formulation may comprise 6-27 wt % of the first pigment, 0.6-5.5 wt % of the second pigment, 0.1-7.0 wt % of the third pigment, 2.0-20.0 wt % of the fourth pigment, or a combination thereof. The color dose formulation may further comprise a filler. The filler comprises silica. The color dose formulation may further comprise a silicon. The silicon may comprise dimethicone, dimethiconol, PEG-dimethicone, dimethicone crosspolymer, and cyclopentasiloxane. The color dose formulation may further comprise a solvent. The solvent may comprise isododecane. The color dose formulation may further comprise a vitamin. The vitamin may comprise tocopherol.

The sunscreen to be mixed with the color dose formulation may be untinted or tinted. The sunscreen may be a cream, paste or fluid dispersion. The sunscreen may comprise a sun filter. The sun filter may be selected from the group consisting of organic filters, inorganic filters and combinations thereof. The sun filter may be selected from the group consisting of butyl methoxydibenzoylmethane; ethylhexyl triazone; terephthalylidene dicamphor sulfonic acid; octocrylene; drometrizole trisiloxane; titanium dioxide; bis-ethylhexyloxyphenol methoxyphenyl triazine; methylene bis-benzotriazolyl tetramethylbutylphenol and polyglycerl-10 laurate; phenylbenzimidazole sulfonic acid; ethylhexyl salicylate; homosalate; silica and titanium dioxide; and combinations thereof.

The sunscreen may further comprise an active compound selected from the group consisting of disodium EDTA, sodium hyaluronate, zinc gluconate, hydrolyzed hyaluronic acid and combinations thereof. The sunscreen may further comprise a fatty compound selected from the group consisting of cetyl alcohol, diisopropyl sebacate, isopropyl lauroyl sarcosinate, stearyl alcohol and combinations thereof. The sunscreen may further comprise a filler selected from the group consisting of silica, silica silylate, perlite and combinations thereof. The sunscreen may further comprise a polymer selected from the group consisting of hydroxypropyl methylcellulose, aluminum starch, xanthan gum, nylon-12, xanthan gum, acrylates/C10-30 alkyl acrylate crosspolymer, acrylates/C10-30 alkyl acrylate crosspolymer, Zea mays (corn) starch, ammonium polyacryloyldimethyl taurate, methyl methacrylate crosspolymer, sodium polyacrylate, poly C10-30 alkyl acrylate, synthetic wax, styrene/acrylates copolymer and combinations thereof. The sunscreen may further comprise a silicon. The silicon may comprise dimethicone. The sunscreen may further comprise a solvent selected from the group consisting of denatured alcohol, alcohol, C12-15 alkyl benzoate, glycerin, pentylene glycol, caprylyl glycol, water, and combinations thereof. The sunscreen may further comprise a surfactant selected from the group consisting of stearic acid; glyceryl stearate and PEG-100 stearate; potassium cetyl phosphate; behenyl alcohol, glyceryl stearate, disodium ethylene dicocamide PEG-15 disulfate and glyceryl stearate citrate; poloxamer 338; inulin lauryl carbamate; and combinations thereof. The sunscreen may further comprise a vegetal extract selected from the group consisting of butylene glycol, *Butyrospermum parkii* (shea) seedcake extract and a combination thereof. The sunscreen may further comprise a vitamin. The vitamin may comprise tocopherol. The sunscreen may further comprise a fragrance. The sunscreen may further comprise a preservative. The preservative may comprise phenoxyethanol.

The customized color shade sunscreen product may have a SPF of 15. The customized color shade sunscreen product may provide an antioxidant effect on a skin when applied to the skin in an effective amount. The customized color shade sunscreen product may protect a skin from infrared rays when applied to the skin in an effective amount. The customized color shade sunscreen product may protect a skin from visible light when applied to the skin in an effective amount. For each method of the present invention, a customized color shade sunscreen product provided by the method is also provided.

A method of preparing a customized color shade sunscreen product is further provided. The preparation method comprises mixing a color dose formulation with a sunscreen, which may be untinted or tinted. As a result, a customized color shade sunscreen product is prepared and matches the skin tone of the subject. The color base composition is selected to match a skin tone of a subject from the group consisting of six color shade compositions: a first color shade composition comprising 26-27 wt % of a first pigment, 0.7-0.8 wt % of a second pigment, 0.2-0.3 wt % of a third pigment, and 5-6 wt % of a fourth pigment; a second color shade composition comprising 26-27 wt % of the first pigment, 0.8-0.9 wt % of the second pigment, 0.1-0.2 wt % of the third pigment, and 2-3 wt % of the fourth pigment; a third color shade composition comprising 22-23 wt % of the first pigment, 1-2 wt % of the second pigment, 0.5-0.6 wt % of the third pigment, and 8-9 wt % of the fourth pigment; a fourth color shade composition comprising 18-19 wt % of the first pigment, 1-2 wt % of the second pigment, 0.5-1.0 wt % of the third pigment, and 12-13 wt % of the fourth pigment; a fifth color shade composition comprising 6-7 wt % of the first pigment, 5-6 wt % of the second pigment, 1-2 wt % of the third pigment, and 19-20 wt % of the fourth pigment; and a sixth color shade composition comprising 8-9 wt % of the second pigment, 6-7 wt % of the third pigment, and 14-15 wt % of the fourth pigment. The first pigment comprises titanium oxide anatase coated with stearoyl aluminum glutamate. The second pigment comprises red iron oxide coated with stearoyl aluminum glutamate. Third pigment comprises black iron oxide coated with aluminum stearoyl glutamate. The fourth pigment comprises yellow iron oxide wrapped with aluminum stearoyl glutamate. The color dose formulation comprises at least 28 wt % totally of the pigments. The six color shade compositions may offer color shades suitable for all skin tones. The six color shade compositions may offer color shades suitable for all six skin phototypes according to the Fitzpatrick scale. The customized color shade sunscreen product may provide a sensorial benefit. The sensorial benefit may be dry touch, good spreadability, no white residues, oil control or a combination thereof.

According to the preparation method, the color dose formulation may comprise 6-27 wt % of the first pigment, 0.6-5.5 wt % of the second pigment, 0.1-7.0 wt % of the third pigment, 2.0-20.0 wt % of the fourth pigment, or a combination thereof. The color dose formulation may comprise a filler, a silicon, a solvent, a vitamin, or a combination thereof. The sunscreen may comprise an active compound, a fatty compound, a filler, a fragrance, a polymer, a preservative, a silicon, a solvent, a sun filter, a surfactant, a vegetal extract, a vitamin, or a combination thereof. The sun filter may be selected from the group consisting of butyl methoxydibenzoylmethane; ethylhexyl triazone; terephthalylidene dicamphor sulfonic acid; octocrylene; drometrizole trisiloxane; titanium dioxide; bis-ethylhexyloxyphenol methoxyphenyl triazine; methylene bis-benzotriazolyl tetramethylbutylphenol and polyglyceryl-10 laurate; phenylbenzimidazole sulfonic acid; ethylhexyl salicylate; homosalate; silica and titanium dioxide; and combinations thereof.

DETAILED DESCRIPTION OF THE INVENTION

The present invention provides customized color shade sunscreen products and preparation thereof. The invention is based on the inventors' surprising discovery of high concentration of pigment blends; unique blends of pigments to develop six different color shades, one for each prototype according to the Fitzpatrick scale; stable formulations for high concentration of pigment blends by unique choices of silicones; and compatibility between the pigment blends and Anthelios sunscreen products. Adding drops of high concentration of pigments to sunscreen products has created color shade sunscreen products that match a wide range of skin tones. According to the present invention, color dose formulations comprising high concentration of pigments of different shades can be customized for the best color fit of sunscreens with different types of skin tones, and bring a big color innovation to the cosmetic market. The customized color shade sunscreen products according to this invention provide excellent product stability and great sunscreen benefits, including high Sun Protection Factor (SPF) values, antioxidant effects, infrared protection, visible light protection, with high-level fillers for matte finish and shine control, sensorial performance (e.g., dry touch, good spreadability, no white residues and oil control) and high level of pigments.

Unless stated otherwise, a wt % figure for an ingredient of a composition is relative to the total weight of the composition.

The term "stable" used herein refers to a physical or chemical property of a cosmetic composition such as a color shade sunscreen product that does not change significantly over time. For example, no significant amount of change (e.g., less than about 10, 5, 1, 0.5 or 0.1 wt %) is observed in precipitation, color, pH, viscosity profile or SEM images for a color shade sunscreen product after storage for a time period of, for example, about 1, 2, 3, 4, 5, 6, 12, 18 or 24 months, at a temperature of about 4-45° C., for example, at room temperature (25° C.) and atmospheric pressure (760 mmHg, i.e., 105 Pa).

The term "subject" used herein refers to a consumer in need of a customized color shade sunscreen product. The consumer may be a human. The subject may have any skin tone.

The present invention provides a method of providing a customized color shade sunscreen product to match a skin tone of a subject, comprising providing a color dose formulation. The present invention also provides a method of providing a customized color shade sunscreen product to match a skin tone of a subject, comprising providing a color dose formulation and an instruction.

The present invention provides a product for providing a customized color shade sunscreen product, comprising a color dose formulation and an instruction. The present invention also provides a product for providing a customized color shade sunscreen product, comprising a color dose formulation, a sunscreen, which may be untinted or tinted, and an instruction.

The present invention provides a method of preparing a customized color shade sunscreen product. The preparation method comprises mixing, for example, 2-4 drops of a selected color dose formulation with a sunscreen, which may be untinted or tinted. The volume ratio of the selected color dose formulation to the sunscreen may be from about 1:20 to 1:0.5. The preparation method may further comprise selecting the color dose formulation to match a skin tone of a subject. As a result, a customized color shade sunscreen product is prepared and matches the skin tone of the subject.

According to the present invention, the instruction provides mixing, for example, 2-4 drops of a selected color dose formulation with a sunscreen, which may be untinted or tinted. The volume ratio of the selected color dose formulation to the sunscreen may be from about 1:20 to 1:0.5. The instruction may further comprise selecting a color dose formulation to match a skin tone of a subject. As a result, a customized color shade sunscreen product is prepared and matches the skin tone of the subject.

The color dose formulation may be in any physical form. For example, the color dose formulation may be a cream, paste or fluid dispersion. The color dose formulation may be in a container such as a tube, jar or bottle.

The color dose formulation may comprise one or more pigments at a total pigment concentration of at least about 20, 25, 28, 30, 33, 35 or 40 wt %. The color dose formulation is suitable for being mixed with a sunscreen to prepare a customized color shade sunscreen product.

The color dose formulation may be selected from various color shade compositions. The color shade compositions may comprise one or more pigments to achieve a desirable color shade. Examples of the color shade compositions include six color shade compositions: a first color shade composition comprising 26-27 wt % of a first pigment, 0.7-0.8 wt % of a second pigment, 0.2-0.3 wt % of a third pigment, and 5-6 wt % of a fourth pigment; a second color shade composition comprising 26-27 wt % of the first pigment, 0.8-0.9 wt % of the second pigment, 0.1-0.2 wt % of the third pigment, and 2-3 wt % of the fourth pigment; a third color shade composition comprising 22-23 wt % of the first pigment, 1-2 wt % of the second pigment, 0.5-0.6 wt % of the third pigment, and 8-9 wt % of the fourth pigment; a fourth color shade composition comprising 18-19 wt % of the first pigment, 1-2 wt % of the second pigment, 0.5-1.0 wt % of the third pigment, and 12-13 wt % of the fourth pigment; a fifth color shade composition comprising 6-7 wt % of the first pigment, 5-6 wt % of the second pigment, 1-2 wt % of the third pigment, and 19-20 wt % of the fourth pigment; and a sixth color shade composition comprising 8-9 wt % of the second pigment, 6-7 wt % of the third pigment, and 14-15 wt % of the fourth pigment. The first pigment may comprise titanium oxide anatase coated with stearoyl aluminum glutamate, and may comprise titanium dioxide, disodium stearoyl glutamate and aluminum hydroxide. The color dose formulation may comprise 6-27 wt % of the first pigment.

The second pigment may comprise red iron oxide coated with stearoyl aluminum glutamate, and may comprise iron oxides, disodium stearoyl glutamate and aluminum hydroxide. The color dose formulation may comprise 0.6-5.5 wt % of the second pigment.

The third pigment may comprise black iron oxide coated with aluminum stearoyl glutamate, and may comprise iron oxides, disodium stearoyl glutamate and aluminum hydroxide. The color dose formulation may comprise 0.1-7.0 wt % of the third pigment.

The fourth pigment may comprise yellow iron oxide wrapped with aluminum stearoyl glutamate, and may comprise iron oxides, disodium stearoyl glutamate and aluminum hydroxide. The color dose formulation may comprise 2.0-20.0 wt % of the fourth pigment.

These six color shade compositions may offer color shades suitable for all skin tones. For example, the six color shade compositions may offer color shades suitable for all six skin phototypes according to the Fitzpatrick scale (also known as Fitzpatrick skin typing test or Fitzpatrick phototyping scale). The Fitzpatrick scale is a well-recognized tool for dermatological research into human skin pigmentation by providing a numerical classification schema for human skin color. There are six categories of the Fitzpatrick scale in relation to the 36 categories of the older von Luschan scale: Type I (scores 0-6) always burns, never tans (pale white; blond or red hair; blue eyes; freckles); Type II (scores 7-13) usually burns, tans minimally (white; fair; blond or red hair; blue, green, or hazel eyes); Type III (scores 14-20) sometimes mild burn, tans uniformly (cream white; fair with any hair or eye color); Type IV (scores 21-27) burns minimally, always tans well (moderate brown); Type V (scores 28-34) very rarely burns, tans very easily (dark brown); and Type VI (scores 35-36) Never burns, never tans (deeply pigmented dark brown to darkest brown). Each of the six color shade compositions may correspond to one of the six skin phototypes according to the Fitzpatrick scale. The selection of a color dose formulation to match a skin tone of a subject may be based on a visual color match between the skin tone and the color shades offered by the color shade compositions. The color shades offered by the color shade compositions may be presented on a printed publication, for example, a chart, photograph, package insert or brochure, or available virtually on, for example, an internet website. The selection may comprise determining the skin phototype on the Fitzpatrick scale for the skin tone and then choosing a color dose formulation corresponding to the skin phototype. The selection may also be made based on the subject's answers to a quiz or questionnaire. The instructions for selecting the color dose formulation may be provided on a printed publication, for example, a chart, photograph, package insert or brochure, or virtually on, for example, an internet website.

In addition to pigments, the color dose formulation may comprise other cosmetically acceptable components such as a filler, a silicon, a solvent and a vitamin.

The color dose formulation may further comprise a filler at, for example, about 0.1-10 wt %, 0.5-5 wt % or 0.5-1.5 wt %. The filler may be any cosmetically acceptable compound suitable for increasing bulk, weight, viscosity, opacity, or strength of the formulation. The filler in the color dose formulation may be chosen from mineral powders like talc, kaolin and silicas, and clays like hectorite and bentonite. For example, the filler in the color dose formulation may comprise silica.

The color dose formulation may further comprise a silicon at, for example, about 1-50 wt %, 10-30 wt % or 20-25 wt %. The silicon may comprise dimethicone, dimethiconol, PEG-10 dimethicone, dimethicone crosspolymer, cyclopentasiloxane, or a combination thereof. For example, the silicon may comprise dimethicone and dimethiconol; PEG-10 dimethicone; dimethicone and dimethicone crosspolymer; or cyclopentasiloxane.

The color dose formulation may further comprise a solvent at, for example, about 1-10 wt %, 3-7 wt % or 4-6 wt %. The solvent may comprise isododecane.

The color dose formulation may further comprise a vitamin at, for example, about 0.1-5 wt %, 0.2-1 wt % or 0.4-0.6 wt %. The vitamin may comprise tocopherol.

The sunscreen may be any untinted or tinted sunscreen. The sunscreen may comprise an active compound, a fatty compound, a filler, a fragrance, a polymer, a preservative, a silicon, a solvent, a sun filter, a surfactant, a vegetal extract, a vitamin and, in case of tinted formulas, pigments, or a combination thereof. The sunscreen may be in any physical form. For example, the sunscreen may be a cream, paste or fluid dispersion. The sunscreen may be in a container such as a tube, jar or bottle.

The sunscreen comprises a sun filter. The sun filter may be selected from the group consisting of butyl methoxydibenzoylmethane; ethylhexyl triazone; terephthalylidene dicamphor sulfonic acid; octocrylene; drometrizole trisiloxane; titanium dioxide; bis-ethylhexyloxyphenol methoxyphenyl triazine; methylene bis-benzotriazolyl tetramethylbutylphenol and polyglyceryl-10 laurate; phenylbenzimidazole sulfonic acid; ethylhexyl salicylate; homosalate; silica and titanium dioxide; and combinations thereof. The sun filter may be an organic filter, an inorganic filter or a combination thereof. The inorganic filter may comprise titanium dioxide. The organic filter may comprise butyl methoxydibenzoylmethane; ethylhexyl triazone; terephthalylidene dicamphor sulfonic acid; octocrylene; drometrizole trisiloxane; bis-ethylhexyloxyphenol methoxyphenyl triazine; methylene bis-benzotriazolyl tetramethylbutylphenol and polyglyceryl-10 laurate; phenylbenzimidazole sulfonic acid; ethylhexyl salicylate; homosalate; silica and titanium dioxide; or a combination thereof.

The sun filter may comprise 2-4 wt % of the butyl methoxydibenzoylmethane; 1-3 wt % of the ethylhexyl triazone; 2-4 wt % of the terephthalylidene dicamphor sulfonic acid; 2-3 wt % of the octocrylene; 0.1-1.0% wt % of the drometrizole trisiloxane; 5-7 wt % of the silica and titanium dioxide; and 1-3 wt % of the methylene bis-benzotriazolyl tetramethylbutylphenol and polyglyceryl-10 laurate; each wt % based on the total weight of the sunscreen.

The sun filter may comprise 0.5-1.5 wt % of the phenylbenzimidazole sulfonic acid; 2-4 wt % of the butyl methoxydibenzoylmethane; 4-6 wt % of the ethylhexyl salicylate; 1-2 wt % of the ethylhexyl triazone; 2-4 wt % of the terephthalylidene dicamphor sulfonic acid; 3-5 wt % of the octocrylene; 8-12 wt % of the drometrizole trisiloxane; and 0.1-1.0 wt % of the bis-ethylhexyloxyphenol methoxyphenyl triazine; each wt % based on the total weight of the sunscreen.

The sun filter may comprise 3-4 wt % of the butyl methoxydibenzoylmethane; 4-5 wt % of the ethylhexyl salicylate; 4-6 wt % of the titanium dioxide; 2-3 wt % of the ethylhexyl triazone; 2-4 wt % of the terephthalylidene dicamphor sulfonic acid; 1-3 wt % of the octocrylene; 0.1-1.0 wt % of the drometrizole trisiloxane; 2-4 wt % of the bis-ethylhexyloxyphenol methoxyphenyl triazine; 8-12 wt % of the silica and titanium dioxide; and 1-3 wt % of the methylene bis-benzotriazolyl tetramethylbutylphenol and polyglyceryl-10 laurate; each wt % based on the total weight of the sunscreen.

The sun filter may comprise 2-4 wt % of the butyl methoxydibenzoylmethane; 4-6 wt % of the ethylhexyl salicylate; 0.5-1.5 wt % of the titanium dioxide; 3-4 wt % of the ethylhexyl triazone; 2-4 wt % of the terephthalylidene dicamphor sulfonic acid; 2-3 wt % of the octocrylene; 5-7 wt % of the homosalate; 2-4 wt % of the drometrizole trisiloxane; and 2-4 wt % of the bis-ethylhexyloxyphenol methoxyphenyl triazine; each wt % based on the total weight of the sunscreen.

The sunscreen may comprise an active compound. The active compound may be any substance that absorbs and/or reflects some of the sun's ultraviolet (UV) radiation. The active compound may be selected from the group consisting of disodium EDTA, sodium hyaluronate, zinc gluconate, hydrolyzed hyaluronic acid and combinations thereof. The active compound may comprise disodium EDTA, sodium hyaluronate, zinc gluconate and disodium EDTA, sodium hyaluronate and hydrolyzed hyaluronic acid; disodium EDTA, and sodium hyaluronate; disodium EDTA, sodium hyaluronate and or disodium EDTA, zinc gluconate. Triethanolamine may be used to adjust the pH of the composition.

The sunscreen may comprise a fatty compound. The fatty compound may be selected from the group consisting of cetyl alcohol, diisopropyl sebacate, isopropyl lauroyl sarcosinate, stearyl alcohol or a combination thereof. The fatty compound may comprise cetyl alcohol, diisopropyl sebacate, isopropyl lauroyl sarcosinate and stearyl alcohol; isopropyl lauroyl sarcosinate; or isopropyl lauroyl sarcosinate and stearyl alcohol.

The sunscreen may comprise a filler. The filler may be any cosmetically acceptable compound suitable for increasing bulk, weight, viscosity, opacity, or strength of the formulation. The filler in the sunscreen may be selected from the group consisting of silica, silica silylate, perlite and combinations thereof. The filler in the sunscreen may comprise silica silylate and perlite; silica and perlite; or silica silylate.

The sunscreen may comprise a polymer. The polymer may be selected from the group consisting of hydroxypropyl methylcellulose, aluminum starch octenylsuccinate, xanthan gum, nylon-12, acrylates/C10-30 alkyl acrylate crosspolymer, acrylates/C10-30 alkyl acrylate crosspolymer, *Zea mays* (corn) starch, ammonium polyacryloyldimethyl taurate, methyl methacrylate crosspolymer, sodium polyacrylate, poly C10-30 alkyl acrylate, synthetic wax, styrene/acrylates copolymer and combinations thereof. The polymer may comprise xanthan gum, *Zea mays* (corn) starch, ammonium polyacryloyldimethyl taurate, poly C10-30 alkyl acrylate; acrylates/C10-30 alkyl acrylate crosspolymer and sodium polyacrylate; hydroxypropyl methylcellulose, aluminum starch octenylsuccinate, nylon-12, ammonium polyacryloyldimethyl taurate, methyl methacrylate crosspolymer and synthetic wax; or aluminum starch octenylsuccinate, xanthan gum, acrylates/C10-30 alkyl acrylate crosspolymer and styrene/acrylates copolymer.

The sunscreen may comprise a silicon. The silicon may comprise dimethicone.

The sunscreen may comprise a solvent. The solvent may be selected from the group consisting of denatured alcohol, alcohol, C12-15 alkyl benzoate, glycerin, pentylene glycol, caprylyl glycol, water, and combinations thereof. The solvent may comprise denatured alcohol, C12-15 alkyl benzoate, caprylyl glycol and water; alcohol, caprylyl glycol and water; or C12-15 alkyl benzoate, glycerin, pentylene glycol, caprylyl glycol and water.

The sunscreen may comprise a surfactant. The surfactant may be selected from the group consisting of stearic acid; glyceryl stearate and PEG-100 stearate; potassium cetyl phosphate; behenyl alcohol, glyceryl stearate, disodium ethylene dicocamide PEG-15 disulfate and glyceryl stearate citrate; poloxamer 338; inulin lauryl carbamate; and combinations thereof. The surfactant may comprise behenyl alcohol, glyceryl stearate, disodium ethylene dicocamide PEG-15 disulfate and glyceryl stearate citrate; poloxamer 338; or inulin lauryl carbamate.

The sunscreen may comprise a vegetal extract. The vegetal extract may comprise butylene glycol and *Butyrospermum parkii* (shea) seedcake extract.

The sunscreen may comprise a vitamin. The vitamin in the sunscreen may comprise tocopherol.

The sunscreen may comprise a preservative. The preservative may comprise phenoxyethanol.

The sunscreen may comprise a fragrance.

According to the method of the present invention, a selected color dose formulation is mixed with a sunscreen, which may be untinted or tinted. For example, 2-4 drops of a color dose formulation may be mixed with a sunscreen to make a homogenous color adapted for one's skin immediately. The volume ratio of a selected color dose formulation to a sunscreen may be from about 1:20 to 1:0.5.

The customized color shade sunscreen product may provide a sensorial benefit. The sensorial benefit may be dry touch, good spreadability, no white residues, oil control or a combination thereof. The customized color shade sunscreen product may have an SPF value no less than the sunscreen used to make the customized color shade sunscreen product according to the invention. The customized color shade sunscreen product may have an SPF value at least similar than the sunscreen used to make the customized color shade sunscreen product according to the invention.

The customized color shade sunscreen product may provide an antioxidant effect on skin when applied to the skin in an effective amount, for example, an amount as recommended for use (e.g., from 2-4 drops). A greater antioxidant effect may be observed on skin by, for example, at least about 5%, 10%, 15%, 20%, 25%, 30%, 40%, 50%, 60%, 70%, 80% or 90%, when the customized color shade sunscreen product is applied to the skin as compared with that on skin without the application. The antioxidant effect may be evaluated in a pollutant model based on an air pollution inhibition effect of a test product having an active ingredient as compared with bare sebum a control product.

The customized color shade sunscreen product may protect skin from infrared rays when applied to the skin in an effective amount. The infrared ray protection may be evidenced by prevention of excess increase in synthesis of metalloproteinase-1 (MMP-1) as induced by infrared radiation. The induced MMP-1 synthesis may be reduced by, for example, at least about 5%, 10%, 15%, 20%, 25%, 30%, 40% or 50%, in skin to which the customized color shade sunscreen product is applied as compared with that in skin without the application. When applied to skin, the customized color shade sunscreen product may inhibit MMP-1 synthesis in the skin by, for example, at least about 5%, 10%, 15%, 20%, 25%, 30%, 40% or 50%, than the sunscreen used to make the customized color shade sunscreen product according to the invention.

The prevention of an excess increase in synthesis of MMP-1 synthesis in skin is directly associated with preservation of collagen in skin.

The customized color shade sunscreen product may protect skin from visible light when applied to the skin in an effective amount. The visible light protection of skin may be evidenced by inhibition of pigmentation induced by visible light in the skin to which the customized color shade sunscreen product is applied. Pigmentation induced by visible light may be inhibited by, for example, at least about 5%, 10%, 15%, 20%, 25%, 30%, 40% or 50%, in skin to which the customized color shade sunscreen product is applied as compared with that in skin without the application.

EXAMPLES

Example 1. Color Dose Formulations

Color dose formulations suitable for this invention comprises a pigment, filler, silicon, solvent, vitamin, silicon or a combination thereof. Four (4) pigments are mixed to generate a limited number (e.g., six color shades) of color shades suitable for matching a wide range of skin tones. The first pigment is titanium oxide anatase coated with stearoyl aluminum glutamate, which comprises titanium dioxide, disodium stearoyl glutamate and aluminum hydroxide. The second pigment is red iron oxide coated with stearoyl aluminum glutamate, which comprises iron oxides, disodium stearoyl glutamate and aluminum hydroxide. The third pigment is black iron oxide coated with aluminum stearoyl glutamate, which comprises iron oxides, disodium stearoyl glutamate and aluminum hydroxide. The fourth pigment is yellow iron oxide wrapped with aluminum stearoyl glutamate, which comprises iron oxides, disodium stearoyl glutamate and aluminum hydroxide. Table 1 shows exemplary color dose formulations, Compositions 1-8, according to this invention.

Example 2. Sunscreens

Sunscreens suitable for this invention comprises an active compound, a fatty compound, a filler, a fragrance, a polymer, a preservative, a silicon, a solvent, a sun filter, a surfactant, a vegetal extract, a vitamin, or a combination thereof. The sun filter comprises butyl methoxydibenzoylmethane; ethylhexyl triazone; terephthalylidene dicamphor sulfonic acid; octocrylene; drometrizole trisiloxane; titanium dioxide; bis-ethylhexyloxyphenol methoxyphenyl triazine; methylene bis-benzotriazolyl tetramethylbutylphenol and polyglyceryl-10 laurate; phenylbenzimidazole sulfonic acid; ethylhexyl salicylate; homosalate; silica and titanium dioxide; or a combination thereof. The sunscreens may be untinted or tinted.

Table 2 shows exemplary untinted sunscreens, Composition 9-16, according to this invention.

Example 3. Anti-Oxidation: Ex-Vivo Test

The anti-oxidation effect of a color shade sunscreen product prepared by mixing a color dose formulation and an untinted sunscreen was evaluated in an ex-vivo test using a "pollutant model" based on cigarette smoke designed to "pollute" the skin sebum after it was collected from volunteer's forehead. The "polluted" skin sebum was further stressed by UVA (5 J/cm$^2$).

Squalene (SQ) and its oxidized products, squalene mono hydroperoxidation (SQOOH), are selected as the analyzing targets in this study to evaluate the SQ oxidation status, which is regarded as an indicator of pollution inhibition effect. Generally, the "polluted" skin sebum exhibits a higher oxidation value than the "clean" skin sebum, which was collected on the equal area of forehead together with the polluted one, and exposed simultaneously under the same UVA dose. The inhibition effect of a formulation with active is calculated by comparing the oxidized SQ of the formulation vs its benchmark. And an overall judgment as Positive effect, Not possible to differentiate or Negative effect will be concluded based on the quantitative inhibition result. Benchmark could be bare sebum or placebo (formula base, without active) depending on the real case.

In this study, color dose Composition 5 (see Table 1) was mixed with untinted sunscreen Compositions 10, 9 or 12 (see Table 2) at a volume ratio of 1:9 for the color dose composition to the sunscreen to make color shade sunscreen Mixtures 1, 2 or 3, respectively.

Compared with bare sebum where no product was applied, Mixture 1 (i.e., 90% of Composition 10+10% of Composition 5) exhibited positive anti-oxidation effect on 6 subjects at an average of 96% with a standard deviation of 1%.

Compared with bare sebum where no product was applied, Mixture 2 (i.e., 90% of Composition 9+10% of Composition 5) exhibited positive anti-oxidation effect on 6 subjects at an average of 78% with a standard deviation of 5%.

Compared with bare sebum where no product was applied, Mixture 3 (i.e., 90% of Composition 12+10% of Composition 5) exhibited positive anti-oxidation effect on 6 subjects at an average of 88% with a standard deviation of 6%.

Example 4. Protective Effect on Visible Light Induced Pigmentation

Assessment of the protective effect of two color shade sunscreen products on visible light induced pigmentation compared with an untreated control zone was carried out in monocentric, investigator-blinded, randomized study with intra-individual comparisons. Untinted sunscreen Composition 9 (see Table 2) was mixed with color shade Composition 2 or 5 (see Table 1) to form color shade sunscreen Mixture 1 or 2, respectively.

Twenty-one (21) subjects were screened. Of them, 20 were randomized and completed the study as planned. The primary objective of the study was to assess the ability of two sunscreen products to prevent the pigmentation induced by visible light. The secondary objectives were to assess the local and overall tolerability of the test products on the basis of adverse event reporting. The Primary endpoint is ITA angle (between the exposed zone (EZ) and the non-exposed one (NEZ)) from D1 to D5 and at D12. The secondary endpoints include delta E (between EZ and NEZ) from D1 to D5 and at D12, colorimetry parameters Delta L*, Delta a* and Delta b* (between EZ and NEZ) from D1 to D5 and at D12, pigmentation score (between EZ and NEZ) from D1 to D5 and at D12, erythema score, and auto-evaluation. At each time-point, the differences Day $i_{i=\{2,3,4,5,12\}}$-Day 1 were analyzed using a linear mixed effect analysis with one within subject factor "Treatment." For each treatment, a linear mixed effect analysis with one within subject factor "Time" was performed as planned in the protocol. Post-hoc comparisons were performed between each evaluation time and baseline using a Dunnett test. Erythema (number of subjects and percentages) were tabulated by severity, by time and by product. If necessary, UEs were tabulated in frequency tables.

All 20 randomized subjects (9 males and 11 females) completed the study normally. The mean age of the subjects was 35 years (range: 24-50 years) and most of them were skin phototype IV (55%).

After exposure, the results showed for the 3 test zones:
 a significant decrease in both the delta ITA° and the delta L* as well as a significant increase in the delta E and the delta a*, from Day 2 to Day 12
 a significant decrease in the delta b from Day 2 to Day 5

Comparisons between the 2 treated zones and the untreated one showed significant differences in favor of the tested products. These results indicate that the pigmentation was significantly more pronounced on the untreated zone. The calculated IP-VL protection indices for Mixture 1 and Mixture 2 are 2.84 and 3.73, respectively.

One subject experienced a doubtful erythema on the untreated zone at Day 2 and another subject experienced a moderate and transient local erythema on the Mixture 2 treated zone at Day 4. Overall, 5 subjects (25.0%) experienced 5 UEs of mild (n=4) to moderate (n=1) intensity.

Under the conditions of this study, the two sunscreen products tested proved their ability to reduce efficiently the pigmentation caused by visible light. All formulations were well-tolerated by the subjects.

Example 5. Prevention Against Infrared-A Radiation Effects

A preclinical study for ex vivo evaluation of efficacy of one color shade sunscreen product on prevention against infrared-A radiation effects was performed by evaluating preclinical efficacy of the product in prevention against photodamage caused by infrared A radiation in human skin culture.

Skin fragments from three healthy subjects were incubated in a culture medium and treated with a color shade sunscreen product prepared by mixing untinted sunscreen Composition 9 (see Table 2) with color dose Composition 5 (see Table 1) at a volume ratio of 1:1.12 for the sunscreen composition to the color dose composition. After 48 hours of incubation, the culture medium and the product were removed and the skin fragments were exposed to a dose of 360 J/cm2 infrared-A radiation using Hydrosun 750 and HBM1 devices (Hydrosun Medizintechnik GmbH, Müllheim, Germany), and then incubated with a fresh culture medium and maintained for 24 hours before collecting the culture supernatant to quantify the concentration of matrix metalloproteinase-1 (MMP-1).

It is known that IR-A radiation produces a significant increase in the production of MMP-1 compared to non-irradiated control (P<0.001), contributing to the process of cutaneous photodamage. The color shade sunscreen product decreased production of MMP-1 compared to IR-A group by 42.49% (P<0.01), indicating a protective effect on skin fragments.

In conclusion, the color shade sunscreen product presented a prophylactic activity against the effects of IR-A radiation compared to only irradiated group, due to the prevention of an excessive increase in the synthesis of MMP-1. This effect is directly associated with the preservation of collagen, a key structure of tissue support, whose commitment contributes to the skin aging process.

The term "about" as used herein when referring to a measurable value such as an amount, a percentage, and the like, is meant to encompass variations of ±20% or 10%, more preferably ±5%, even more preferably ±1%, and still more preferably ±0.1% from the specified value, as such variations are appropriate.

Although the invention is illustrated and described herein with reference to specific embodiments, the invention is not intended to be limited to the details shown. Rather, various modifications may be made in the details within the scope and range of equivalents of the claims without departing from the invention.

TABLE 1

Exemplary color dose formulations

| Cosmetic Type | Chemical Name | INCI US | 1 | 2 | 3 | 4 | 5 | 6 | 7 | 8 |
|---|---|---|---|---|---|---|---|---|---|---|
| Pigment | Oxyde De Titane Anatase Enrobe De Stearoyl Glutamate: D'aluminium (97/3) (Cl: 77891) | Titanium Dioxide (And) Disodium Stearoyl Glutamate (And) Aluminum Hydroxide | 26.99 | 26.52 | 22.565 | 18.394 | 6.183 | 0 | 25.99 | 6.233 |
| Pigment | Oxyde De Fer Rouge Enrobe, De Stearoyl Glutamate D'aluminium (3%) | Iron Oxides (And) Disodium Stearoyl Glutamate (And) Aluminum Hydroxide | 0.71 | 0.82 | 1.607 | 1.783 | 5.093 | 8.28 | 0.71 | 5.043 |
| Pigment | Oxyde De Fer, Noir Enrobe De Stearoyl Glutamate D'aluminium (3%) | Iron Oxides (And) Disodium Stearoyl Glutamate (And) Aluminum Hydroxide | 0.28 | 0.18 | 0.535 | 0.743 | 1.783 | 6.97 | 0.78 | 1.783 |
| Pigment | Oxyde De Fer Jaune Enrobe De Stearoyl Glutamate D'aluminium (3%) | Iron Oxides And) Disodium Stearoyl Glutamate (And) Aluminum Hydroxide | 5.02 | 2.48 | 8.293 | 12.08 | 19.941 | 14.75 | 5.52 | 19.941 |
| Filler | Amorphous Silica Microspheres (5 μm) | Silica | 1 | 1 | 1 | 1 | 1 | 1 | 1 | 1 |
| Silicon | Melange Poly Dimethylsiloxane, Alpha Omega Dihydroxyle/ Poly Dimethylsiloxane 5 Cst. | Dimethicone (And) Dimethiconol | 3 | 3 | 3 | 3 | 3 | 3 | 3 | 3 |
| Silicon | Poly Dimethylsiloxane Oxyethylene (Dp: 70- Viscosite: 500 Cst) | Peg-10 Dimethicone | 2 | 2 | 2 | 2 | 2 | 2 | 2 | 2 |

TABLE 1-continued

Exemplary color dose formulations

| Cosmetic Type | Chemical Name | INCI US | 1 | 2 | 3 | 4 | 5 | 6 | 7 | 8 |
|---|---|---|---|---|---|---|---|---|---|---|
| Silicon | Mix Of Polydimethyl-siloxane Reticuled By Hexadiene/Poly Dimethylsiloxane | Dimethicone: (And) Dimethicone Crosspolymer | 19 | 19 | 19 | 19 | 19 | 19 | 19 | 19 |
| Solvent | Isododecane | Isododecane | 4 | 6 | 4 | 4 | 4 | 6 | 6 | 4 |
| Vitamin | Vitamin, E : DI-Alpha-Tocopherol | Tocopherol | 0.5 | 0.5 | 0.5 | 0.5 | 0.5 | 0.5 | 0 5 | 0.5 |
| Silicon | Cyclopenta Dimethylsiloxane | Cyclopentasiloxane | 37.5 | 38.5 | 37.5 | 37.5 | 37.5 | 38.5 | 38.5 | 37.5 |

TABLE 2

Exemplary untinted sunscreens

| Cosmetic Type | Chemical name | INCI US | 9 | 10 | 11 | 12 | 13 | 14 | 15 | 16 |
|---|---|---|---|---|---|---|---|---|---|---|
| Active Compound | Ethylene Diamine Tetracetic Acid, Disodic Salt, 2 $H_2O$ | Disodium EDTA | 0.1 | 0.097 | 0.1 | 0.097 | 0.12 | 0.099 | 0.1 | 0.097 |
| Active Compound | Hyaluronate De Sodium (Pm : 1.100.000) En Poudre | Sodium Hyaluronate | 0.04 | 0 | 0 | 0 | 0.03 | 0 | 0 | 0 |
| Active Compound | Gluconate De Zinc | Zinc Gluconate | 0.01 | 0 | 0 | 0.001 | 0.01 | 0 | 0 | 0.021 |
| Active Compound | Triethanolamine | Triethanolamine | 0.46 | 2.05 | 1.25 | 0.77 | 0.45 | 2.01 | 1.25 | 0.75 |
| Active Compound | Acide Hyaluronique De Bas Poids Moleculaire (50 Kda) | Hydrolyzed Hyaluronic Acid | 0 | 0.02 | 0 | 0 | 0 | 0.04 | 0 | 0 |
| Fatty Compound | Cetyl Alcohol | Cetyl Alcohol | 0.5 | 0 | 0 | 0 | 0.5 | 0 | 0 | 0 |
| Fatty Compound | Diisopropyl Sebacate | Diisopropyl Sebacate | 5 | 0 | 0 | 0 | 5 | 0 | 0 | 0 |
| Fatty Compound | Isopropyl N-Lauroylsarcosinate | Isopropyl Lauroyl Sarcosinate | 2.5 | 0.5 | 0.5 | 0.5 | 2.5 | 0.5 | 0.5 | 0.5 |
| Fatty Compound | Stearyl Alcohol | Stearyl Alcohol | 0 | 0 | 0.4 | 0.5 | 0 | 0 | 0.4 | 0.5 |
| Filler | AMORPHOUS SILICA MICROSPHERES (5 µM) | SILICA | 0 | 1 | 0 | 4 | 0 | 1 | 0 | 4 |
| Filler | Hexamethyldisiloxane Treated Silica Gel (Free Flowing Powder) | Silica Silvlate | 0.5 | 0 | 0.5 | 0 | 0.5 | 0 | 0.5 | 0 |
| Filler | EXPANDED PERLITE (25 µm) | PERLITE | 0.01 | 1 | 0 | 1 | 0.01 | 1 | 0 | 1 |
| Fragrance | Fragrance | Fragrance | 0.5 | 0 | 0.5 | 0 | 0.5 | 0 | 0.5 | 0 |
| Polymer | Hydroxypropyl Methyl Cellulose | Hydroxypropyl Methylcellulose | 0 | 0 | 0.1 | 0 | 0 | 0 | 0.1 | 0 |
| Polymer | Amidon De Mais Esterifie Par Anhydride Octenylsuccinique Sel D'aluminium | Alumninom Starch Octenylsuccinate | 0 | 0 | 2 | 3 | 0 | 0 | 2 | 3 |
| Polymer | Gomme, De Xanthane | Xanthan Gum | 0 | 0 | 0 | 0.1 | 0 | 0 | 0 | 0.1 |
| Polymer | Poudre De Nylon 12 | Nylon-12 | 0 | 0 | 1 | 0 | 0 | 0 | 1 | 0 |
| Polymer | Xanthane: Polysaccharides: Glucose/Mannose/Acide Glucuronique (40/30/30) | Xanthan Gum | 0.25 | 0 | 0 | 0 | 0.25 | 0 | 0 | 0 |

TABLE 2-continued

Exemplary untinted sunscreens

| Cosmetic Type | Chemical name | INCI US | 9 | 10 | 11 | 12 | 13 | 14 | 15 | 16 |
|---|---|---|---|---|---|---|---|---|---|---|
| Polymer | Copolymere Acide Acrylique/Methacrylate De Stearyle Polymerise Dans Un Melange Acetate D'ethyle/Cyclohexane | Acrylates/C10-30 Alkyl Acrylate Crosspolymer | 0 | 0.15 | 0 | 0 | 0 | 0.15 | 0 | 0 |
| Polymer | Polymere Carboxyvinyllique Synthetise Dans Le Melange Acetate D'ethyle/Cyclohexane | Acrylates/C10-30 Alkyl Acrylate Crosspolymer | 0 | 0 | 0 | 0.25 | 0 | 0 | 0 | 0.25 |
| Polymer | Amidon De Mais | Zea Mays (Corn) Starch | 2 | 0 | 0 | 0 | 2 | 0 | 0 | 0 |
| Polymer | Acide Poly Acrylamidomethyl Propane Sulfonique Neutralise Partiellement A L'ammoniaque Et Hautement Reticule | Ammonium Polyacryloyidimethyl Taurate | 0.7 | 0 | 0.5 | 0 | 0.7 | 0 | 0.5 | 0 |
| Polymer | Spheres Crouses De Poly Methacrylate De Methyle (10 Microns) | Methyl Methacrylate Crosspolymer | 0 | 0 | 1 | 0 | 0 | 0 | 1 | 0 |
| Polymer | Polyacrylate De Sodium | Sodium Polyacrylate | 0 | 1 | 0 | 0 | 0 | 1 | 0 | 0 |
| Polymer | Poly Acrylate D'alkyle | Poly C10-30 Alkyl Acrylate | 2 | 0 | 0 | 0 | 2 | 0 | 0 | 0 |
| Polymer | Cire De Polymethylène De Point De Fusion Environ 60° C. | Synthetic Wax | 0 | 0 | 1 | 0 | 0 | 0 | 1 | 0 |
| Polymer | Hollow Styrene/Acrylates Copolymer Spheres | Styrene/Acrylates Copolymer | 0 | 0 | 0 | 4 | 00 | 0 | 0 | 4 |
| Preservative | 2-Phenoxyethanol | Phenoxyethanol | 0.6 | 0.6 | 0.6 | 0.7 | 0.6 | 0.6 | 0.6 | 0.7 |
| Silicon | Poly Dimethylsiloxane (Viscosite: 10 Cst) | Dimethicone | 0 | 0 | 2.5 | 1 | 0 | 0 | 2.5 | 1 |
| Silicon | Poly Dimethysiloxane (Viscosite: 5 Cst) | Dimethicone | 0 | 3 | 0 | 0 | 0 | 3 | 0 | 0 |
| Solvent | Denatured Absolute Ethyl Alcohol | Alcohol Denat. | 5 | 0 | 0 | 0 | 5 | 0 | 0 | 0 |
| Solvent | Non-Denatured Absolute Ethyl Alcohol | Alcohol | 0 | 15 | 00 | 0 | 0 | 15 | 0 | 0 |
| Solvent | Deionized Water In According To The Microbiological Norme | Water | 20 | 2 | 11.15 | 25 | 20 | 2 | 11.15 | 25 |
| Solvent | C12-15 Alkyl Benzoate | C12-15 Alkyl Benzoate | 2.5 | 0 | 7.5 | 2 | 2.5 | 0 | 7.5 | 2 |
| Solvent | Glycerin | Glycerin | 0 | 0 | 2 | 1.1225 | 0 | 0 | 2 | 1.1225 |
| Solvent | Pentane-1,2-Diol | Pentylene Glycol | 0 | 0 | 2 | 2 | 0 | 0 | 2 | 2 |
| Solvent | Octane-1,2-Diol | Caprylyl Glycol | 0.4 | 0.4 | 0.3 | 0.4 | 0.4 | 0.4 | 0.3 | 0.4 |
| Solvent | La Roche Posay, Water Preparation | Water | 2 | 2 | 2 | 2 | 2 | 2 | 2 | 2 |
| Sun Filter | 2-Phenyl-1h-Benzimidazole-5-Sulphonic Acid | Phenylbenzimidazole Sulfonic Acid | 0 | 1 | 0 | 0 | 0 | 2 | 0 | 0 |

TABLE 2-continued

Exemplary untinted sunscreens

| Cosmetic Type | Chemical name | INCI US | 9 | 10 | 11 | 12 | 13 | 14 | 15 | 16 |
|---|---|---|---|---|---|---|---|---|---|---|
| Sun Filter | 1-[4-(1,1-Dimethylethyl)Phenyl]-3-(4-Methoxyphenyl)Propane-1,3-Dione | Butyl Methoxy-dibenzolymethane | 3 | 3 | 3.5 | 3 | 3 | 4 | 3.5 | 3.4 |
| Sun Filter | 2-Ethylhexyl Salicylate | Ethylhexyl Salicylate | 0 | 5 | 4.5 | 5 | 0 | 3 | 4.5 | 5 |
| Sun Filter | Rutile Titanium Dioxide (15 Nm) Coated With Stearic Acid And Aluminum Hydroxide | Titanium Dioxide | 0 | 0 | 5 | 1 | 0 | 0 | 5 | 1 |
| Sun Filter | Tris(2-Ethylhexyl)-4,4',4''-(1,3,5-Trazine-2,4,6-Triyltrilmino)Tribenzoate | Ethylhexyl Triazone | 2 | 1.2 | 2.5 | 3.5 | 1 | 1.2 | 2.5 | 3.1 |
| Sun Filter | (E-E)-3,3' (1,4-Phenylenedimethyl-Idene)-Bis(2-Oxobornane-10-Sulfonic Acid As 32% In Aqueous Solution | Terephthalylide Dicamphor Sulfonic Acid | 3 | 3 | 3 | 3 | 2 | 3 | 2 | 3 |
| Sun Filter | 2-Ethylhexyl 2-Cyano-3,3-Diphenylacrylate | Octocrylene | 2.5 | 4 | 2 | 2.5 | 3.5 | 4 | 2.2 | 3.5 |
| Sun Filter | Homomenthyl Salicylate | Homosalate | 0 | 0 | 0 | 6 | 0 | 0 | 0 | 6 |
| Sun Filter | 2-(2-H-Benzotriazole-2-Y1)-4-Methyl-6-[2-Methyl-3-[1,3,3,3-Tetramethyl-1-[(Trimethylsilyl)Oxy]Disiloxanyl]Propyl]Phenol | Drometrizole Trisiloxane | 0.5 | 10 | 0.5 | 3 | 1.5 | 10 | 0.3 | 2 |
| Sun Filter | Phenol, 2,2'-[6-Methoxyphenyl)-1,3,5-Triazine-2.4-Diy( )Bis[5-[(2-Ethylhexyl)Oxy]- | Bis-Ethylhexyl-oxypbenol Methoxyphenyl Triazine | 0 | 0.5 | 3 | 3 | 0 | 0.5 | 3.5 | 3 |
| Sun Filter | TITANIUM DIOXIDE ENCAPSULATED IN SILICA MICROSPHERES (SILICE/T102 (55/45), 2-7 μm) | SILICA (And) TITANIUM DIOXIDE | 6 | 0 | 10 | 0 | 6 | 0 | 10.5 | 0 |
| Sun Filter | 2,2'-Methylenebis[6-(2h-Benzotriazol-2-Y1)-4-(1,1,3,3 Tetramethyl-Butyl)Phenol] In Water Dispersion Preserved | Methylene Bis-Benzotriazolyl Tetramethylbutyl-phenol (And) Polyglyceryl-10 Laurate | 2 | 0 | 2 | 0 | 2 | 0 | 2 | 0 |
| Surfactant | Acides Gras (Acide Stearique Majoritaire) D'origine Vegetale | Stearic Acid | 0 | 0 | 1.5 | 0 | 0 | 0 | 1.5 | 0 |
| Surfactant | Melange Mono/Distearate De Glyceryle/ Stearate De Polyethylene Glycol (100 Oe) | Glyceryl Stearate (And) Peg-100 Stearate | 0 | 0 | 1.3 | 0 | 0 | 0 | 1.3 | 0 |
| Surfactant | Phosphate De Mono-Cetyle Mono-Potassique Non Stabilise | Potassium Cetyl Phosphate | 0 | 0 | 1 | 1 | 0 | 0 | 1 | 1 |

TABLE 2-continued

Exemplary untinted sunscreens

| Cosmetic Type | Chemical name | INCI US | 9 | 10 | 11 | 12 | 13 | 14 | 15 | 16 |
|---|---|---|---|---|---|---|---|---|---|---|
| Surfactant | Melange Ethyldiamido-N-Cocoyl Sulfonate De Sodium Ethoxyle (15oe)/Alcool Behenylique/Stearate/Citrate De Glyceryle | Behenyl Alcohol (And) Glyceryl Stearate (And) Disodium Ethylene Dicocamide Peg-15 Disulfate (And) Glyceryl Stearate Citrate | 3 | 0 | 0 | 0 | 3 | 0 | 0 | 0 |
| Surfactant | Condensat D'oxyde D'ethylene Et D'oxyde De Propylene Et D'oxyde D'ethylene (Pm: 14000) (128 Oe/54 Op/128 Oe) | Poloxamer 338 | 0 | 0.05 | 0.5 | 0 | 0 | 0.05 | 0.5 | 0 |
| Surfactant | Inulin Lauryl Carbamate In Glycerin | Inulin Lauryl Carbamate | 0 | 0 | 0 | 1.17 | 0 | 0 | 0 | 1.17 |
| Vegetal Extract | Shea Butter Hydro-Butylene Glycol Extract | Butylene Glycol (And) Butyrospermum Parkil (Shea) Seedcake Extract | 0 | 0.25 | 0 | 0 | 0 | 0.25 | 0 | 0 |
| Vitamin | Vitamin E: DI-Alpha-Tocopherol | Tocopherol | 0 | 0.05 | 0.3 | 0.1 | | 0.05 | 0.3 | 0.1 |
| Solvent | Deionized Water In According To The Microbiological Norme | Water | 32.93 | 43.133 | 22.5 | 19.2895 | 32.93 | 43.133 | 22.5 | 19.2895 |

The invention claimed is:

1. A product for providing a customized color shade sunscreen product, comprising:
   a. a color dose formulation selected to match a skin tone of a subject from a group consisting of six color shade compositions:
      i. a first color shade composition comprising 26-27 wt % of a first pigment, 0.7-0.8 wt % of a second pigment, 0.2-0.3 wt % of a third pigment, and 5-6 wt % of a fourth pigment;
      ii. a second color shade composition comprising 26-27 wt % of the first pigment, 0.8-0.9 wt % of the second pigment, 0.1-0.2 wt % of the third pigment, and 2-3 wt % of the fourth pigment;
      iii. a third color shade composition comprising 22-23 wt % of the first pigment, 1-2 wt % of the second pigment, 0.5-0.6 wt % of the third pigment, and 8-9 wt % of the fourth pigment;
      iv. a fourth color shade composition comprising 18-19 wt % of the first pigment, 1-2 wt % of the second pigment, 0.5-1.0 wt % of the third pigment, and 12-13 wt % of the fourth pigment;
      v. a fifth color shade composition comprising 6-7 wt % of the first pigment, 5-6 wt % of the second pigment, 1-2 wt % of the third pigment, and 19-20 wt % of the fourth pigment; and
      vi. a sixth color shade composition comprising 8-9 wt % of the second pigment, 6-7 wt % of the third pigment, and 14-15 wt % of the fourth pigment;
   wherein the first pigment comprises titanium oxide anatase coated with stearoyl aluminum glutamate, the second pigment comprises red iron oxide coated with stearoyl aluminum glutamate, the third pigment comprises black iron oxide coated with aluminum stearoyl glutamate, and the fourth pigment comprises yellow iron oxide wrapped with aluminum stearoyl glutamate;
   wherein the color dose formulation comprises at least 28 wt % totally of the pigments; and
   wherein the color dose formulation is suitable for being mixed with a sunscreen to prepare a customized color shade sunscreen product; and
   b. an instruction comprising mixing the selected color dose formulation with the sunscreen, whereby a customized color shade sunscreen product is prepared and matches the skin tone of the subject.

2. A product for providing a customized color shade sunscreen product, comprising:
   a. a color dose formulation selected to match a skin tone of a subject from a group consisting of six color shade compositions:
      i. a first color shade composition comprising 26-27 wt % of a first pigment, 0.7-0.8 wt % of a second pigment, 0.2-0.3 wt % of a third pigment, and 5-6 wt % of a fourth pigment;
      ii. a second color shade composition comprising 26-27 wt % of the first pigment, 0.8-0.9 wt % of the second pigment, 0.1-0.2 wt % of the third pigment, and 2-3 wt % of the fourth pigment;
      iii. a third color shade composition comprising 22-23 wt % of the first pigment, 1-2 wt % of the second pigment, 0.5-0.6 wt % of the third pigment, and 8-9 wt % of the fourth pigment;

iv. a fourth color shade composition comprising 18-19 wt % of the first pigment, 1-2 wt % of the second pigment, 0.5-1.0 wt % of the third pigment, and 12-13 wt % of the fourth pigment;

v. a fifth color shade composition comprising 6-7 wt % of the first pigment, 5-6 wt % of the second pigment, 1-2 wt % of the third pigment, and 19-20 wt % of the fourth pigment; and vi. a sixth color shade composition comprising 8-9 wt % of the second pigment, 6-7 wt % of the third pigment, and 14-15 wt % of the fourth pigment;

wherein the first pigment comprises titanium oxide anatase coated with stearoyl aluminum glutamate, the second pigment comprises red iron oxide coated with stearoyl aluminum glutamate, the third pigment comprises black iron oxide coated with aluminum stearoyl glutamate, and the fourth pigment comprises yellow iron oxide wrapped with aluminum stearoyl glutamate;

wherein the color dose formulation comprises at least 28 wt % totally of the pigments; and b. a sunscreen; and c. an instruction comprising mixing the selected color dose formulation with the sunscreen at a volume ratio from 1:10 to 10:1, whereby a customized color shade sunscreen product is prepared and matches the skin tone of the subject.

3. The product of claim 1, wherein the instruction further comprises selecting the color dose formulation to match the skin tone of the subject.

4. The product of claim 1, wherein the six color shade compositions offer color shades suitable for all skin tones.

5. The product of claim 1, wherein the six color shade compositions offer color shades suitable for all six skin phototypes according to the Fitzpatrick scale.

6. The product of claim 1, wherein the customized color shade sunscreen product provides a sensorial benefit selected from the group consisting of dry touch, good spreadability, no white residues and oil control.

7. The product of claim 1, wherein the color dose formulation comprises 6-27 wt % of the first pigment, 0.6-5.5 wt % of the second pigment, 0.1-7.0 wt % of the third pigment, 2.0-20.0 wt % of the fourth pigment, or a combination thereof.

8. The product of claim 1, wherein the color dose formulation further comprises a filler, wherein the filler comprises silica.

9. The product of claim 1, wherein the color dose formulation further comprises a silicon, wherein the silicon comprises dimethicone, dimethiconol, PEG-10 dimethicone, dimethicone crosspolymer, and cyclopentasiloxane.

10. The product of claim 1, wherein the color dose formulation further comprises a solvent, wherein the solvent comprises isododecane.

11. The product of claim 1, wherein the color dose formulation further comprises a vitamin, wherein the vitamin comprises tocopherol.

12. The product of claim 1, wherein the color dose formulation is a cream, paste or fluid dispersion.

13. The product of claim 1, wherein the sunscreen comprises a sun filter.

14. The product of claim 13, wherein the sun filter is selected from the group consisting of organic filters, inorganic filters and combinations thereof.

15. The product of claim 13, wherein the sun filter is selected from the group consisting of butyl methoxydibenzoylmethane; ethylhexyl triazone; terephthalylidene dicamphor sulfonic acid; octocrylene; drometrizole trisiloxane; titanium dioxide; bis-ethylhexyloxyphenol methoxyphenyl triazine; methylene bis-benzotriazolyl tetramethylbutylphenol and polyglyceryl-10 laurate; phenylbenzimidazole sulfonic acid; ethylhexyl salicylate; homosalate; silica and titanium dioxide; and combinations thereof.

16. The product of claim 1, wherein the sunscreen further comprises an active compound selected from the group consisting of disodium EDTA, sodium hyaluronate, zinc gluconate, hydrolyzed hyaluronic acid and combinations thereof.

17. The product of claim 1, wherein the sunscreen further comprises a fatty compound selected from the group consisting of cetyl alcohol, diisopropyl sebacate, isopropyl lauroyl sarcosinate, stearyl alcohol and combinations thereof.

18. The product of claim 1, wherein the sunscreen further comprises a filler selected from the group consisting of silica, silica silylate, perlite and combinations thereof.

19. The product of claim 1, wherein the sunscreen further comprises a polymer selected from the group consisting of hydroxypropyl methylcellulose, aluminum starch, xanthan gum, nylon-12, xanthan gum, acrylates/C10-30 alkyl acrylate crosspolymer, acrylates/C10-30 alkyl acrylate crosspolymer, *Zea mays* (corn) starch, ammonium polyacryloyldimethyl taurate, methyl methacrylate crosspolymer, sodium polyacrylate, poly C10-30 alkyl acrylate, synthetic wax, styrene/acrylates copolymer and combinations thereof.

20. The product of claim 1, wherein the sunscreen further comprises a silicon, wherein the silicon comprises dimethicone.

21. The product of claim 1, wherein the sunscreen further comprises a solvent selected from the group consisting of denatured alcohol, alcohol, C12-15 alkyl benzoate, glycerin, pentylene glycol, caprylyl glycol, water, and combinations thereof.

22. The product of claim 1, wherein the sunscreen further comprises a surfactant selected from the group consisting of stearic acid; glyceryl stearate and PEG-100 stearate; potassium cetyl phosphate; behenyl alcohol, glyceryl stearate, disodium ethylene dicocamide PEG-15 disulfate and glyceryl stearate citrate; poloxamer 338; inulin lauryl carbamate; and combinations thereof.

23. The product of claim 1, wherein the sunscreen further comprises a vegetal extract selected from the group consisting of butylene glycol, *Butyrospermum parkii* (shea) seedcake extract and a combination thereof.

24. The product of claim 1, wherein the sunscreen further comprises a vitamin, wherein the vitamin comprises tocopherol.

25. The product of claim 1, wherein the sunscreen further comprises a fragrance.

26. The product of claim 1, wherein the sunscreen further comprises a preservative, wherein the preservative comprises phenoxyethanol.

27. The product of claim 1, wherein the sunscreen is a cream, paste or fluid dispersion.

28. The product of claim 1, wherein the customized color shade sunscreen product has a SPF of 15.

29. The product of claim 1, wherein the customized color shade sunscreen product provides an antioxidant effect on a skin when applied to the skin in an effective amount.

30. The product of claim 1, wherein the customized color shade sunscreen product protects a skin from infrared rays when applied to the skin in an effective amount.

31. The product of claim 1, wherein the customized color shade sunscreen product protects a skin from visible light when applied to the skin in an effective amount.

32. A method of preparing a customized color shade sunscreen product, comprising mixing a color dose formulation with a sunscreen, wherein the color dose formulation is selected to match a skin tone of a subject from a group consisting of six color shade compositions:
   a. a first color shade composition comprising 26-27 wt % of a first pigment, 0.7-0.8 wt % of a second pigment, 0.2-0.3 wt % of a third pigment, and 5-6 wt % of a fourth pigment;
   b. a second color shade composition comprising 26-27 wt % of the first pigment, 0.8-0.9 wt % of the second pigment, 0.1-0.2 wt % of the third pigment, and 2-3 wt % of the fourth pigment;
   c. a third color shade composition comprising 22-23 wt % of the first pigment, 1-2 wt % of the second pigment, 0.5-0.6 wt % of the third pigment, and 8-9 wt % of the fourth pigment;
   d. a fourth color shade composition comprising 18-19 wt % of the first pigment, 1-2 wt % of the second pigment, 0.5-1.0 wt % of the third pigment, and 12-13 wt % of the fourth pigment;
   e. a fifth color shade composition comprising 6-7 wt % of the first pigment, 5-6 wt % of the second pigment, 1-2 wt % of the third pigment, and 19-20 wt % of the fourth pigment; and
   f. a sixth color shade composition comprising 8-9 wt % of the second pigment, 6-7 wt % of the third pigment, and 14-15 wt % of the fourth pigment;
   wherein the first pigment comprises titanium oxide anatase coated with stearoyl aluminum glutamate, the second pigment comprises red iron oxide coated with stearoyl aluminum glutamate, the third pigment comprises black iron oxide coated with aluminum stearoyl glutamate, and the fourth pigment comprises yellow iron oxide wrapped with aluminum stearoyl glutamate;
   wherein the color dose formulation comprises at least 28 wt % totally of the pigments;
   whereby a customized color shade sunscreen product is prepared and matches the skin tone of the subject.

33. The method of claim 32, further comprising selecting the color shade formulation from the group consisting of the six color shade compositions.

34. The method of claim 32, wherein the six color shade compositions offer color shades suitable for all skin tones.

35. The method of claim 32, wherein the six color shade compositions offer color shades suitable for all six skin phototypes according to the Fitzpatrick scale.

36. The method of claim 32, wherein the customized color shade sunscreen product provides a sensorial benefit comprising dry touch, good spreadability, no white residues, oil control or a combination thereof.

37. The method of claim 32, wherein the color dose formulation comprises 6-27 wt % of the first pigment, 0.6-5.5 wt % of the second pigment, 0.1-7.0 wt % of the third pigment, 2.0-20.0 wt % of the fourth pigment, or a combination thereof.

38. The method of claim 32, wherein the color dose formulation comprises a filler, a silicon, a solvent, a vitamin, or a combination thereof.

39. The method of claim 32, wherein the sunscreen comprises an active compound, a fatty compound, a filler, a fragrance, a polymer, a preservative, a silicon, a solvent, a sun filter, a surfactant, a vegetal extract, a vitamin, or a combination thereof.

40. The method of claim 39, wherein the sun filter is selected from the group consisting of butyl methoxydibenzoylmethane; ethylhexyl triazone; terephthalylidene dicamphor sulfonic acid; octocrylene; drometrizole trisiloxane; titanium dioxide; bis-ethylhexyloxyphenol methoxyphenyl triazine; methylene bis-benzotriazolyl tetramethylbutylphenol and polyglyceryl-10 laurate; phenylbenzimidazole sulfonic acid; ethylhexyl salicylate; homosalate; silica and titanium dioxide; and combinations thereof.

* * * * *